US00PP12317P2

(12) United States Plant Patent
Vandenberg

(10) Patent No.: US PP12,317 P2
(45) Date of Patent: Jan. 1, 2002

(54) CHRYSANTHEMUM PLANT NAMED 'YOCOCOA BEACH'

(75) Inventor: Cornelis P. Vandenberg, Salinas, CA (US)

(73) Assignee: Yoder Brothers, Inc., Barberton, OH (US)

( * ) Notice: Subject to any disclaimer, the term of this patent is extended or adjusted under 35 U.S.C. 154(b) by 0 days.

(21) Appl. No.: 09/525,655

(22) Filed: Mar. 15, 2000

(51) Int. Cl.[7] ..... A01H 5/00
(52) U.S. Cl. ..... Plt./286
(58) Field of Search ..... Plt./286, 296

*Primary Examiner*—Howard J. Locker
(74) *Attorney, Agent, or Firm*—C. A. Whealy

(57) ABSTRACT

A distinct cultivar of Chrysanthemum plant named 'Yococoa Beach', characterized by its upright and uniformly mounded plant habit; freely branching, dense and full plants; strong dark green foliage; uniform flowering; early flowering, eight-week response time; ability to be grown as either disbudded or center budded plants; very freely flowering with about seven inflorescences per lateral stem; large daisy-type inflorescences that are about 8.5 cm in diameter; dark orange bronze-colored ray florets with variable yellow bases and bright yellow disc florets; and excellent postproduction longevity with inflorescences and leaves maintaining good substance and color for more than three weeks in an interior environment.

2 Drawing Sheets

BACKGROUND OF THE INVENTION

The present Invention relates to a new and distinct cultivar of Chrysanthemum plant, botanically known as *Dendranthema grandiflora* and hereinafter referred to by the cultivar name Yococoa Beach.

The new Chrysanthemum is a product of a planned breeding program conducted by the Inventor in Salinas, Calif. and Fort Myers, Fla. The objective of the breeding program is to create new potted Chrysanthemum cultivars with desirable inflorescence form and floret colors, good substance, and excellent postproduction longevity.

The new Chrysanthemum originated from a cross made by the Inventor in October, 1994, in Salinas, Calif., of a proprietary Chrysanthemum seedling selection identified as YB-5547 as the male, or pollen, parent with the Chrysanthemum commercial cultivar Rage, disclosed in U.S. Plant Pat. No. 8,770, as the female, or seed, parent. The new Chrysanthemum was discovered and selected by the Inventor in Fort Myers, Fla., as a single flowering plant within this population in November, 1995. The selection of this plant was based on its desirable inflorescence form and floret colors.

Asexual reproduction of the new Chrysanthemum by terminal cuttings harvested in a controlled environment in Fort Myers, Fla., has shown that the unique features of this new Chrysanthemum are stable and reproduced true to type in successive generations.

SUMMARY OF THE INVENTION

The cultivar Yococoa Beach has not been observed under all possible environmental conditions. The phenotype may vary somewhat with variations in environment such as temperature, daylength and light intensity, without, however, any variance in genotype.

The following traits have been repeatedly observed and are determined to be the unique characteristics of 'Yococoa Beach'. These characteristics in combination distinguish 'Yococoa Beach' as a new and distinct Chrysanthemum:

1. Upright and uniformly mounded plant habit.
2. Freely branching, dense and full plants.
3. Strong dark green foliage.
4. Uniform flowering.
5. Early flowering, eight-week response time.
6. Ability to be grown as either disbudded or center budded plants.
7. Very freely flowering; about seven inflorescences per lateral stem.
8. Large daisy-type inflorescences that are about 8.5 cm in diameter.
9. Dark orange bronze-colored ray florets with variable yellow bases and bright yellow disc florets.
10. Excellent postproduction longevity with inflorescences and leaves maintaining good substance and color for more than three weeks in an interior environment.

Compared to plants of the culitvar, Mobile, disclosed in U.S. Plant Pat. No. 9,335, plants of the are different in the following characteristics:

1. Plants of the new Chrysanthemum are more upright than plants of the cultivar Mobile.
2. Plants of the new Chrysanthemum have a more attractive inflorescence form than plants of the cultivar Mobile.
3. Ray florets of plants of the new Chrysanthemum are more orange and have less yellow coloration at the base than ray florets of plants of the cultivar Mobile which are more red in color.
4. Disc florets of plants of the new Chrysanthemum are slower to mature and maintain their immature green coloration longer than disc florets of plants of the cultivar Mobile.

BRIEF DESCRIPTION OF THE PHOTOGRAPHS

The accompanying colored photographs illustrate the overall appearance of the new Chrysanthemum showing the colors as true as it is reasonably possible to obtain in colored reproductions of this type. Colors in the photographs may differ from the color values cited in the detailed botanical description which more accurately describe the actual colors of the new Chrysanthemum.

The photograph at the top of the first sheet comprises a side perspective view of a typical flowering plant of 'Yococoa Beach'.

The photograph at the bottom of the first sheet comprises a close-up view of upper (left) and lower (right) surfaces of typical inflorescences and upper (left) and lower (right) surfaces of typical leaves of the cultivar Yococoa Beach.

The photograph at the top of the second sheet comprises a side perspective view of typical flowering plants of 'Yococoa Beach' (left) and 'Mobile' (right).

The photograph at the bottom of the second sheet comprises a close-up view of typical inflorescences of plants of 'Yococoa Beach' (left) and 'Mobile' (right).

DETAILED BOTANICAL DESCRIPTION

In the following description, color references are made to The Royal Horticultural Society Colour Chart except where general terms of ordinary dictionary significance are used. The following observations and measurements describe plants grown and flowered during the Autumn in Leamington, Ontario, Canada, under greenhouse conditions which approximate those generally used in commercial potted Chrysanthemum production. Four unrooted cuttings were directly stuck in a 15-cm container and pinched once. Plants used for this description were grown as center budded-types. Measurements and numerical values represent averages of typical flowering plants.

Botanical classification: *Dendranthema grandiflora* cultivar Yococoa Beach.

Commercial classification: Daisy center budded-type potted Chrysanthemum.

Parentage:

*Male, or pollen, parent.*—Proprietary Chrysanthemum seedling selection identified as YB-5547.

*Female, or seed, parent.*—Commercial Chrysanthemum cultivar Rage, disclosed in U.S. Plant Pat. No. 8,770.

Propagation:

*Type.*—Terminal tip cuttings.

*Time to rooting.*—Seven to ten days with soil temperatures of 21° C.

*Rooting habit.*—Fine, fibrous and well-branched.

Plant description:

*Appearance.*—Herbaceous daisy potted Chrysanthemum which can be grown as either disbudded or center budded plants. Inverted triangle; stems mostly upright and somewhat outwardly spreading giving a uniformly mounded appearance to the plant. Freely branching; about three to four lateral branches develop after removal of terminal apex (pinching); dense and full plants.

*Plant height.*—About 32 cm.

*Plant width.*—About 37 cm.

*Foliage description.*—Arrangement: Alternate. Length: About 7.3 cm. Width: About 6.8 cm. Apex: Cuspidate. Base: Cuneate to truncate. Margin: Palmately lobed, sinuses between lateral lobes mostly divergent. Texture: Upper and lower surfaces with very fine pubescence; veins prominent on lower surface. Petiole length: About 2.3 cm. Petiole diameter: About 2.5 mm. Color: Young foliage upper surface: 147A. Young foliage lower surface: Darker than 147B. Mature foliage upper surface: 147A. Mature foliage lower surface: 147B. Venation upper surface: 147A to 147B. Venation lower surface: 147B.

Inflorescence description:

*Appearance.*—Daisy inflorescence form with elongated oblong-shaped ray florets. Inflorescences borne on terminals above foliage. Disk and ray florets arranged acropetally on a capitulum.

*Flowering response.*—Under natural conditions, plants flower in the autumn/winter in the Northern Hemisphere. At other times of the year, inflorescence initiation and development can be induced under short day/long night conditions (at least 13.5 hours of darkness). Plants exposed to three weeks of long day/short night conditions after planting followed by photoinductive short day/long night conditions flower about eight weeks later; early flowering.

*Postproduction longevity.*—Inflorescences and leaves maintain good color and substance for more than three weeks in an interior environment.

*Quantity of inflorescences.*—Very freely flowering; about seven inflorescences per lateral stem and about 25 inflorescenses per plant.

*Inflorescence bud.*—Height: About 7 mm. Diameter: About 9 mm. Color: Darker than 144A.

*Inflorescence size.*—Diameter: About 8.5 cm. Depth (height): About 2 cm. Diameter of disc: About 1.8 cm.

*Ray florets.*—Shape: Elongated-oblong. Orientation: Initially upright, then about 30 to 45° to horizontal. Length: About 4.1 cm. Width: About 1.3 cm. Apex: Cuspidate to emarginate. Margin: Entire. Texture: Smooth, glabrous, satiny. Number of ray florets per inflorescence: About 26. Color: When opening: Close to 45A. Fully opened, upper surface: Yellow, 9A, overlaid with red, 45A, giving orange bronze appearance, close to, but darker than 34B; base, yellow, 9A. Amount of yellow coloration depends on light intensity and temperature. Fully opened, lower surface: Mostly yellow, 9A, with faint reddish, close to 45A, longitudinal streaks; base, close to 6A.

*Disc florets.*—Shape: Tubular. Apex: Serrated. Length: About 6 mm. Width: Apex: About 1.5 mm. Base: About 1 mm. Number of disc florets per inflorescence: About 224. Color: Immature: 144A. Mature: Apex: Yellow, 7A. Mid-section: Light green, 154A. Base: White, 155D.

*Peduncles.*—Aspect: Angled about 40 to 45° to stem. Length: First peduncle: About 4.1 cm. Fourth peduncle: About 7.5 cm. Diameter: About 2.5 mm. Texture: Pubescent. Color: 146A.

*Reproductive organs.*—Androecium: Present on disc florets only. Anther color: 9A. Pollen amount: Scarce. Pollen color: 12A. Gynoecium: Present on both ray and disc florets.

Disease resistance: Resistance to pathogens common to Chrysanthemum has not been observed on plants grown under commercial greenhouse conditions.

Seed production: Seed production has not been observed.

It is claimed:

1. A new and distinct cultivar of Chrysanthemum plant named 'Yococoa Beach', as illustrated and described.

* * * * *

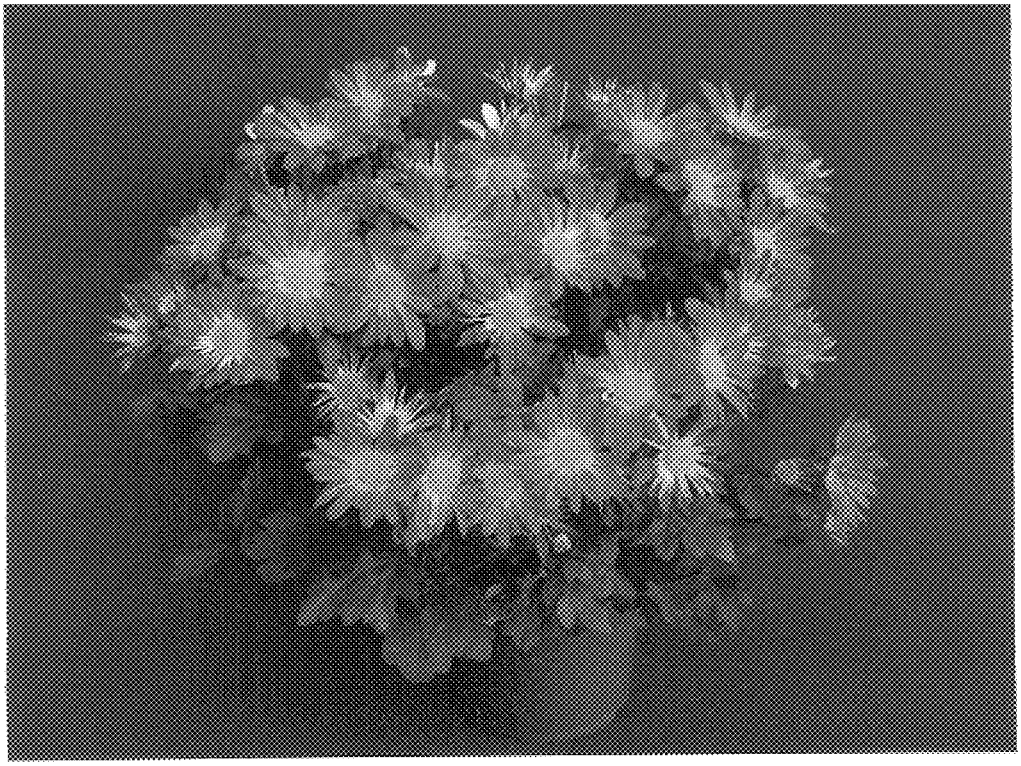
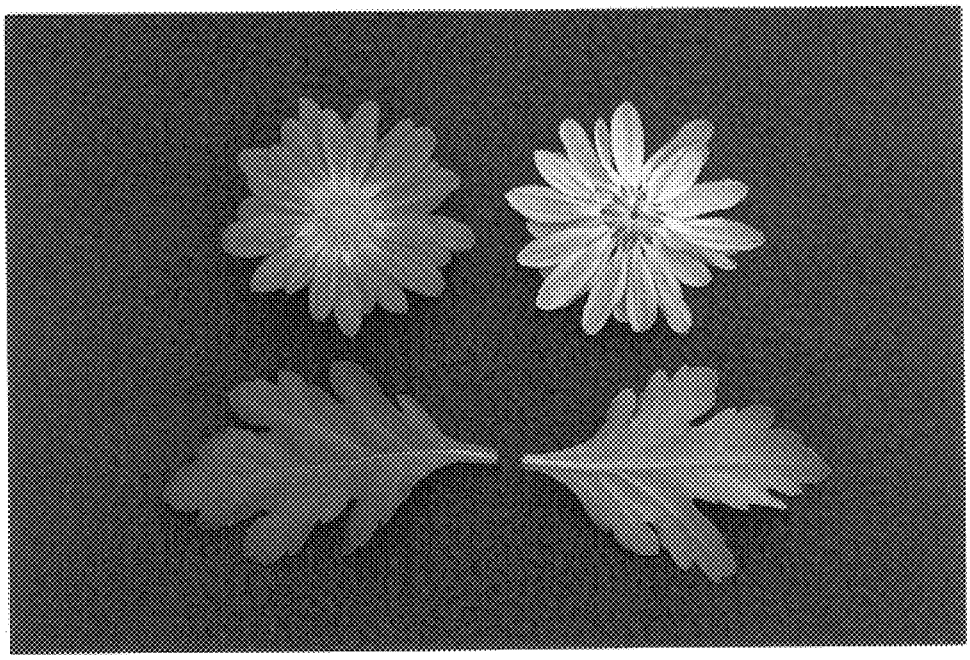

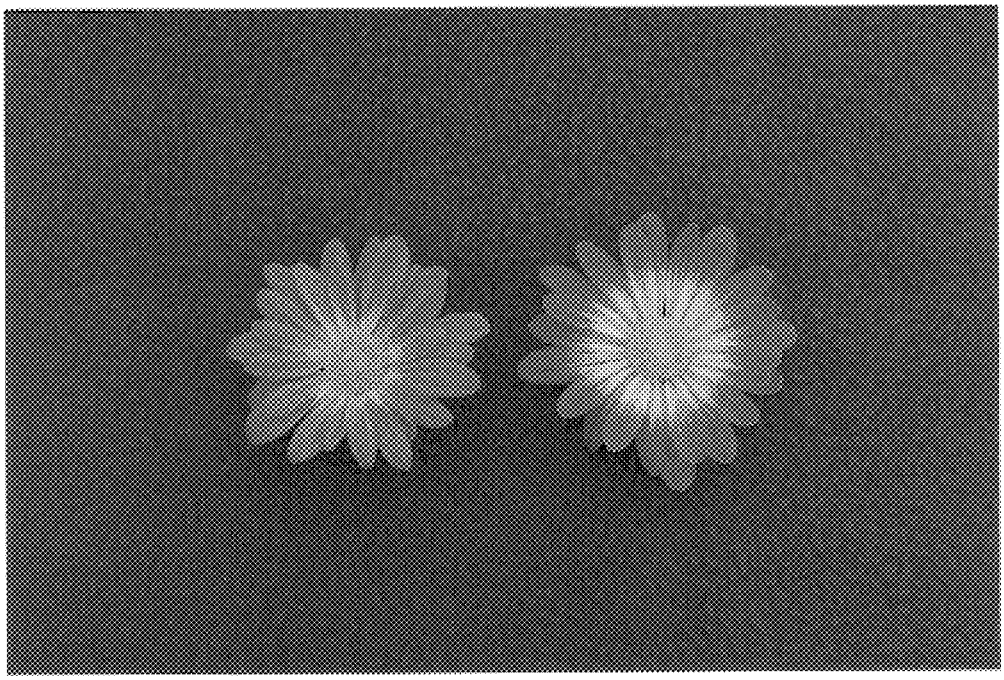

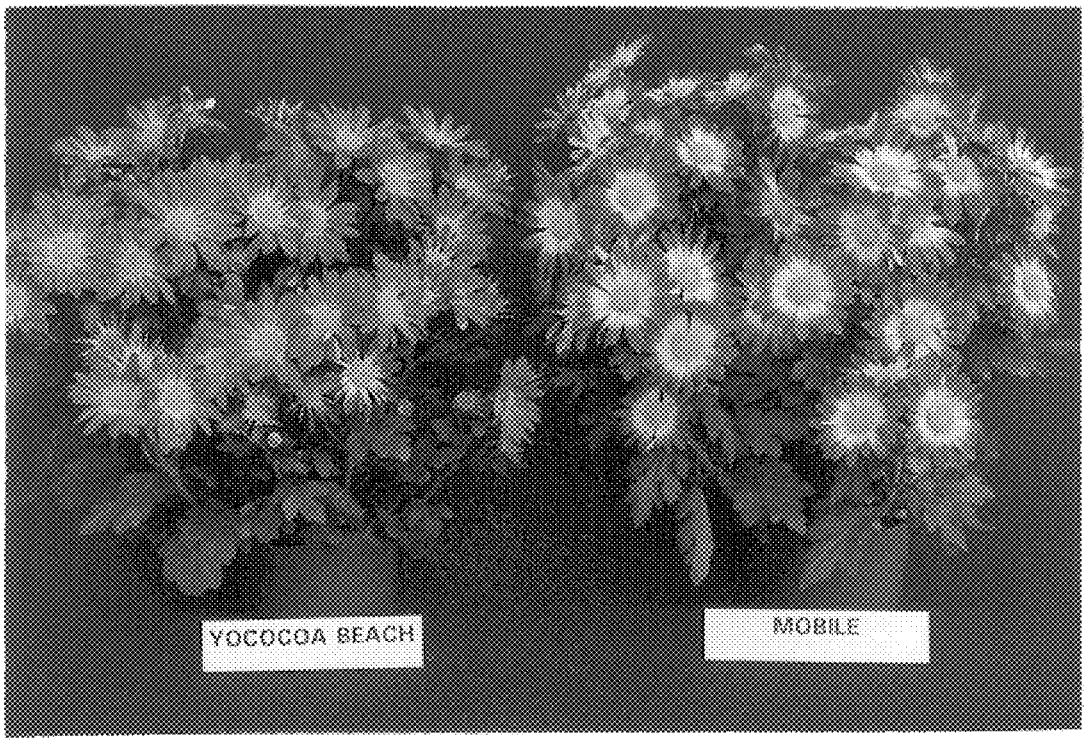
YOCOCOA BEACH
MOBILE